United States Patent
Sheehy et al.

(10) Patent No.: US 10,344,574 B2
(45) Date of Patent: Jul. 9, 2019

(54) METHOD FOR INCREASING RECOVERY OF OIL FROM CARBONATE OIL RESERVOIRS UTILIZING AN "IN SITU" ORGANIC APPROACH

(71) Applicant: TITAN OIL RECOVERY, INC., Beverly Hills, CA (US)

(72) Inventors: Alan James Sheehy, Minyama (AU); Michael Thomas Carroll, Glendora, CA (US); Colin Kenneth Hill, San Dimas, CA (US); Brian W. G. Marcotte, Rolling Hills, CA (US)

(73) Assignee: Titan Oil Recovery, Inc., Beverly Hills, CA (US)

( * ) Notice: Subject to any disclaimer, the term of this patent is extended or adjusted under 35 U.S.C. 154(b) by 0 days.

(21) Appl. No.: 15/311,096

(22) PCT Filed: May 20, 2015

(86) PCT No.: PCT/US2015/031814
§ 371 (c)(1),
(2) Date: Nov. 14, 2016

(87) PCT Pub. No.: WO2015/179545
PCT Pub. Date: Nov. 26, 2015

(65) Prior Publication Data
US 2017/0089186 A1 Mar. 30, 2017

Related U.S. Application Data

(60) Provisional application No. 62/000,786, filed on May 20, 2014.

(51) Int. Cl.
| | |
|---|---|
| *E21B 43/22* | (2006.01) |
| *E21B 43/16* | (2006.01) |
| *E21B 43/20* | (2006.01) |
| *C09K 8/582* | (2006.01) |
| *C12Q 1/6888* | (2018.01) |
| *E21B 47/00* | (2012.01) |
| *E21B 49/02* | (2006.01) |

(52) U.S. Cl.
CPC .............. *E21B 43/16* (2013.01); *C09K 8/582* (2013.01); *C12Q 1/6888* (2013.01); *E21B 43/20* (2013.01); *E21B 47/00* (2013.01); *E21B 49/02* (2013.01)

(58) Field of Classification Search
CPC . C09K 8/582; C09K 8/62; C09K 8/58; C09K 8/592; C09K 2208/24; E21B 43/16; E21B 43/164; E21B 43/00; E21B 43/20; E21B 2049/085

See application file for complete search history.

(56) References Cited

U.S. PATENT DOCUMENTS

| | | | |
|---|---|---|---|
| 4,971,151 A * | 11/1990 | Sheehy | C09K 8/905 166/246 |
| 2001/0045279 A1 | 11/2001 | Converse et al. | |
| 2011/0067856 A1 | 3/2011 | Kohr | |
| 2011/0146973 A1 | 6/2011 | Olguin Lora et al. | |
| 2012/0122740 A1 | 5/2012 | Roldan Carrillo et al. | |
| 2012/0261117 A1 | 10/2012 | Pavia et al. | |
| 2014/0367087 A1 * | 12/2014 | Sheehy | C09K 8/582 166/246 |
| 2015/0053407 A1 * | 2/2015 | Voordouw | E21B 43/16 166/303 |

FOREIGN PATENT DOCUMENTS

| | | |
|---|---|---|
| WO | 2013113126 A1 | 8/2013 |
| WO | 2014205061 A1 | 12/2014 |
| WO | 2014205087 A1 | 12/2014 |

OTHER PUBLICATIONS

International Searching Authority, "Notification of Transmittal of The International Search Report and The Written Opinion of the International Searching Authority", for PCT/US2015/031814, dated Aug. 7, 2015, 7 pages.

European Extended Search Report, "Communication of the Extended Search Report and Search Opinion" by the European Patent Office in Munich, Germany, for European Application No. 15796881.9, dated Nov. 13, 2017, 11 pages.

* cited by examiner

*Primary Examiner* — Zakiya W Bates
(74) *Attorney, Agent, or Firm* — Zarley Law Firm, P.L.C.

(57) ABSTRACT

A method of increasing oil recovery form a carbonate oil reservoir by determining the presence of microorganisms, determining a specific nutrient package to stimulate the microorganisms, delivering the nutrient package to the carbonate oil reservoir, and allowing the stimulated microorganisms to change the adhesion tension between the carbonate oil rock formation and the oil and the water.

15 Claims, No Drawings

METHOD FOR INCREASING RECOVERY OF OIL FROM CARBONATE OIL RESERVOIRS UTILIZING AN "IN SITU" ORGANIC APPROACH

BACKGROUND OF THE INVENTION

This invention is directed to a method of recovering oil from carbonate oil reservoirs. More specifically, this invention is directed to a method of recovering oil from carbonate rock using an "in situ" organic approach.

Known in the art are processes using nutrient stimulation to increase oil production from sandstone oil reservoirs. In contrast, microorganisms needed for the nutrient stimulation process, historically were not known or rarely recovered from oil bearing carbonate rock structures. Moreover, there is no known evidence that any microorganisms seen had or have oil interactive properties.

Based on discoveries in sandstone reservoirs where a change in oil water interaction, as a result of stimulation of oil interactive form of microorganisms, results in more oil released for ultimate recovery, a method for accomplishing the same in carbonate oil reservoirs is needed. More specifically, a method of determining the presence of microorganisms in carbonate reservoirs is needed that also demonstrates that such microorganisms can be converted to hydrophobic form. Such conversion would alter oil water interaction in the carbonate rock structure releasing more oil into the flow channels for production.

An objective of the present invention is to provide a method of increasing oil recovery from carbonate oil reservoirs.

Another objective of the present invention is to provide a method of determining the presence of microorganisms in carbonate reservoirs.

A still further objective of the present invention is to provide a method that alters oil water interaction in carbonate rock structures to release more oil in flow channels.

These and other objectives will be apparent to those skilled in the art based upon the following written description.

SUMMARY OF THE INVENTION

A method of increasing oil recovery from carbonate reservoirs includes the steps of determining the presence of microorganisms in the carbonate oil reservoir. The determination is made by taking one or more samples from a study well and analyzing the sample. Also a specific nutrient package is formulated that causes a reaction with the microorganisms.

Once the nutrient package is delivered to the carbonate oil reservoir where the nutrient package stimulates and/or modifies surface active properties of the resident microorganisms. The stimulated microorganisms then interact with the carbonate rock formations to change the adhesion tension between the rock formation and the water and the oil. This change includes altering the contact angle of oil to rock which makes the formation of droplets more likely. The method works in part with carbonate oil rock formations which have very small or no pores because of fractures and/or microfractures that allow a water flood to work through a second porosity of rock formation and not through pore spaces.

About 50 percent of all oil is found in carbonate reservoirs throughout the world. Until recently, it was believed that very few, if any, microorganisms existed in these carbonate rock formations. Based on discoveries in sandstone reservoirs, we present a method for improving recovery of oil from carbonate rock oil reservoirs by an "in situ" method of detecting, and stimulating resident microorganism that results in the alteration of the oil water interaction of the fluid-rock interface in the reservoir. This change in oil water interaction changes fluid-rock interaction from oil-wet to water-wet resulting in more oil release from the rock structure. In a further embodiment where carbonate structures were believed to be basically devoid of microorganisms, the invention describes how the Method not only can stimulate naturally occurring microorganisms but also those resident microorganisms in the carbonate rock structure that were introduced during drilling and development activities of the oil well as well as subsequent water flooding. Sampling from the proposed "in situ" study-well and performing an analysis either on site or in the laboratory achieve the detection of microorganisms and the determination that species are present that will react to specific nutrient/chemical stimulation. The initial sample preferably is transported from the well to a laboratory for analysis. During transport, the sample conditions are maintained as close as possible to reservoir conditions to provide more accurate laboratory analysis.

A series of analyses of the sample are conducted that lead to the formulation of a specific nutrient package that is both compatible with the unique conditions in carbonate oil reservoir and has been shown to stimulate the resident microorganism population. A genetic analysis of resident microorganisms may also be conducted to aid in the determination of the nutrient package to be used and to determine the rate at which nutrients will be added to the reservoir.

The delivery of the nutrient package is used in the "in situ" study to modify and/or stimulate certain members of the resident microbe population found in the reservoir. The delivery of the nutrient package in the chosen "in situ" well further permits a subsequent and critical microbiological response analysis under actual reservoir conditions examining the response and changes in resident microorganisms with the intent of optimizing the recovery of oil.

In the course of these "in situ" studies one form of the nutrient package has been shown to suppress some undesirable microorganisms while stimulating desirable resident microorganisms. In an alternative form, the modification of the population through delivery of the nutrient package increases the number of resident microorganisms having surface-active properties allowing the organisms to become interactive with the oil in the reservoir. In still yet another form, the stimulation of certain resident microbes by the delivery of the nutrient package is followed by a specific nutrient limitation that induces certain subgroups in the population to reduce interfacial tension between oil and water, alter fluid rock wettability and to change capillarity forces to improve oil flow and ultimate recovery of oil as a percent of oil in place.

While the nutrient package includes different compositions and forms, preferably the nutrient package is prepared in a liquid form that is both stable and resistant to unwanted microbial growth until it is diluted into the water flood and to take advantage of water flood reservoirs. Further, the specific preferred nutrient package consists of a group of non-glucose, soluble nutrients. Finally, the preferred nutrient package is stable across a wide range of salinities and temperatures commonly found in carbonate oil bearing rock structures.

The amount and frequency of stimulation of certain resident microbes through the delivery of a nutrient package is to a sufficient level that the surface-active properties improve oil flow in the reservoir and ultimately oil recovery as manifested by increased oil production and ultimate total oil recovery from the oil reservoir.

In a further preferred embodiment, the nutrient package is supplemented on a periodic basis into the injected water flooding source water over a period of time determined from microorganism response and concentration in monitoring samples taken at the "in Situ" well. The cycling may be as frequent as every 6 weeks or long as 18 months between cycles. Very specifically, the nutrient supplementation is not supplied on a continuous basis—only periodically as indicated by laboratory analysis and well performance over time.

In another embodiment the method can stimulate resident microorganisms in mature water floods in cooler zones or less salty zones created as a result of the water flooding in environments that are otherwise too hot to or too salty to generally support microorganism growth and survival such that improved release of oil from such reservoirs is effectively facilitated.

What is claimed is:

1. A method of recovering oil from carbonate oil reservoirs, comprising the steps of:
   delivering a nutrient package that is chemically stable across widely variable salinities and temperatures to a carbonate oil reservoir to stimulate resident microorganisms; and
   allowing the stimulated resident microorganisms to interact with carbonate oil rock formations to change adhesion tension of the carbonate oil rock formation from oil-wet to water-wet.

2. The method of claim 1 further comprising the step of limiting availability of the nutrient package to induce some of the stimulated resident microorganisms to reduce interfacial tension between oil and water.

3. The method of claim 1 wherein the delivery of the nutrient package increases a population of stimulated resident microorganisms having surface active properties that allow the stimulated resident microorganisms to interact with oil.

4. The method of claim 1 further comprising the step of selecting a nutrient package that is in liquid form, stable, and resistant to unwanted microbial growth until diluted in water.

5. The method of claim 1 wherein the nutrient package is comprised of non-glucose soluble nutrients.

6. The method of claim 1 further comprising the step of supplementing the delivery of the nutrient package on a periodic basis into an injected water flooding source water over a period of time.

7. The method of claim 1 wherein adhesion tension is changed such that a contact angle of the oil to the carbonate oil rock is changed making formation of droplets more likely.

8. The method of claim 1 further comprising the step of determining a presence of microorganisms in the carbonate oil reservoir.

9. The method of claim 8 wherein the step of determining a presence of microorganisms includes taking a sample from a study well and analyzing the sample.

10. The method of claim 9 wherein the analysis is done on site.

11. The method of claim 9 wherein the sample is transported from the study well to a lab while maintain sample conditions close to reservoir conditions.

12. The method of claim 9 further comprising the step of formulating the nutrient package based on the analysis.

13. The method of claim 9 further comprising the step of determining the nutrient package based upon a genetic analysis.

14. The method of claim 9 further comprising the step of determining a rate at which the nutrient package is delivered to the carbonate, oil reservoir.

15. The method of claim 1 wherein resident microorganisms are selected from a group consisting of naturally occurring microorganisms, microorganisms introduced during drilling and development, and microorganisms introduced during subsequent water flooding.

* * * * *